June 28, 1949. J. D. BROWNELL Plant Pat. 849
ROSE PLANT
Filed April 22, 1946
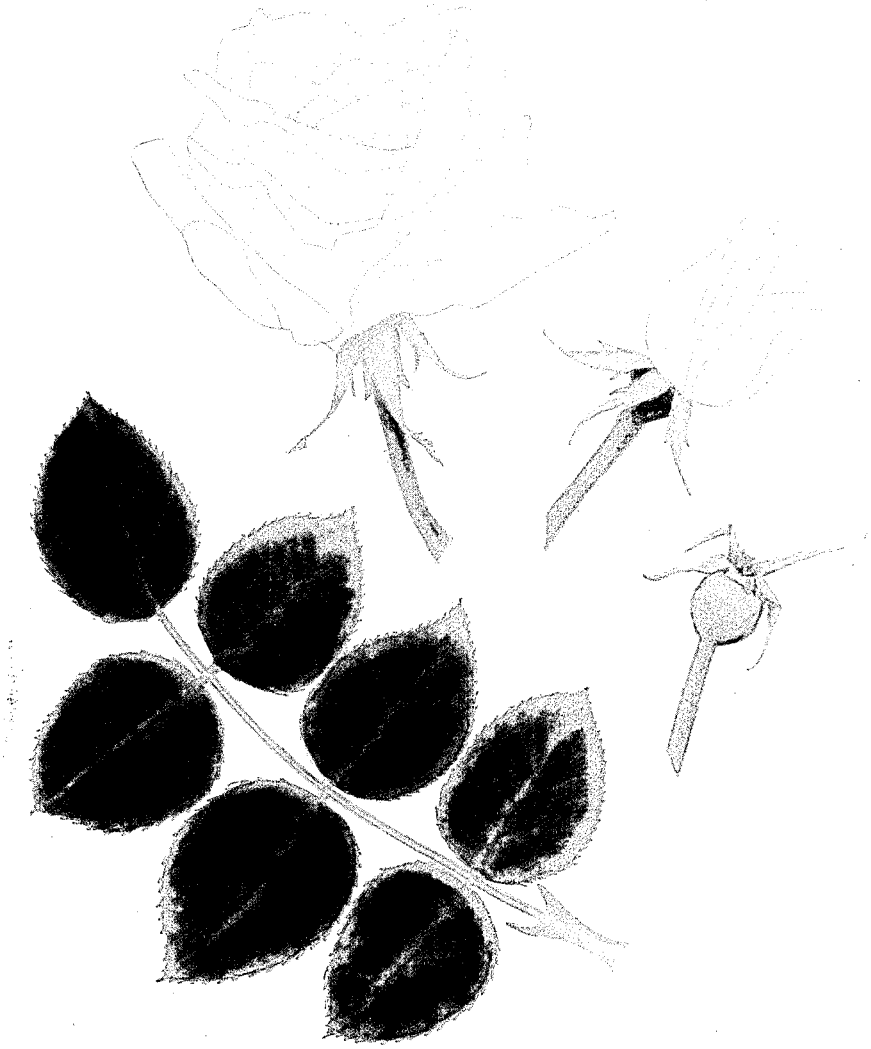
Josephine D. Brownell.
INVENTOR
BY
ATTORNEY Patented June 28, 1949

Plant Pat. 849

UNITED STATES PATENT OFFICE

849

ROSE PLANT

Josephine D. Brownell, Little Compton, R. I.

Application April 22, 1946, Serial No. 663,872

1 Claim. (Cl. 47—61)

My invention relates to roses and especially to a new, original and distinct variety of the class known commercially as "hybrid teas" and is a variant in that class, being a *Rosa wichuraiana* hybrid tea produced by me and under my direction in the breeding grounds of my research gardens in Little Compton, Rhode Island, by cross pollenation, which can be and has been asexually reproduced.

My new rose is new as to the following characteristics and especially as to their joint association with the characteristics inherited from *Rosa wichuraiana,* of hardiness, or immunity from serious injury on account of cold temperatures prevailing in certain parts of the northern United States, and of special vigor, bloom quality and foliage resistance:

The red to pink shades (ordinary dictionary definition) of its petals and the yellow overlay on both sides, in combination with the unique brilliance thereof and their tendency to hold these colors under exposure;

The novelty and variation within certain definite limits of the form of the bloom, its character of holding that form for a long time, and the petallage of the flowers;

Its character of fragrance;

Its unusual abundance of flowers;

The intensity of its remontant and everblooming or reblooming character;

Its character of ascending in height by recurrent branching and progressively longer stems from the base in some instances long enough to be classified as canes;

The character of producing many seven leafleted leaves; which character seldom has obtained on hybrid teas not having *Rosa wichuraiana* ancestry, but frequently obtains on flower stems of descendants of *Rosa wichuraiana* of the dwarf reblooming type;

And especially its characteristic of partial freedom from premature defoliation by black-spot, under certain definite conditions of exposure, without any cultural control.

In the accompanying drawing forming a part of this specification I have shown my new rose in its natural colors, that is as near as is possible to do so artificially.

My new rose is otherwise described as follows:

*Essential information*

Type: Hybrid tea, *Rose wichuraiana* hybrid, dwarf ascending to tall to climber, for garden display, cut flower and forcing or growing under glass.

Class: Hybrid tea crossed with *Rosa wichuraiana,* further restricted by originator to include only those varieties that can survive moderately low sub-zero temperatures.

Breeding: This variety was produced and bred by me and under my direction by cross pollenation.

The genealogy of my new rose variety is as follows: Pollen was from the variety Anne Vanderbilt. The seed parent was produced by me and under my direction by first producing a pollen parent by crossing Gruss an Teplitz with Golden Climber Mrs. A. C. James, and a seed parent by crossing General Jacqueminot with Dr. W. Van Fleet. A seedling therefrom was used as a seed parent crossed with Frau Karl Druschki. A seedling therefrom was used as a seed parent crossed with Etoile de Holland; a seedling therefrom was the seed parent that produced my new rose variety.

The pollenation that fertilized the seed that grew into this new rose, as well as the pollenation that produced several of its parents were directed by me and were performed by emasculating flowers and placing thereon a bag protecting them from self and foreign pollen. These bags were later removed and the flowers were hand pollenated with a camel's hair brush and the bags immediately replaced. The date of this final pollenation was July 3, 1941.[1] The seed was planted under my direction on December 4, 1941, and the date of the first flower was July 12, 1942.

The plant and flower seemed to be of unusual merit and I have since made and directed extensive propagations and tests thereof.

Plants of this variety budded from this seedling on to *Rosa multiflora* root stock, have after being exposed to moderate sub-zero temperatures, survived and bloomed normally the following season in the hybrid tea manner. The variety has been propagated by budding at Little Compton, Rhode Island, in the months of July and August in 1942–45 inclusive and the characters have successively reproduced, true to the original seedling.

*Flower*

Habit: It blooms out of doors in Little Compton, beginning about three days prior to the average beginning time of commercial hybrid teas and continues relative to growth of the plant until frost.

Flowers borne: Often one and frequently two or three and occasionally more on each stem, in the usual hybrid tea type of cluster. The pedicels and peduncles are medium in diameter and length, erect, stiff, almost smooth, free from large prickles and bristles but with several very small prickles varying to small rigid hairs of the same color as the prickles lower down on the stem. Stems are long, medium to

[1] This and other dates herein are approximate.

slightly large in diameter, and notably stiff and rigid.

Quantity of bloom: Free to abundant, being cumulative in quantity from year to year as the plant increases in size, notably free flowering through the summer.

Fragrance: Medium, strong, distinctive, pleasing China tea in combination with that of *Rosa wichuraiana*, under favorable environment, especially in warm dry weather.

Bud: Neck normal as described, opens well, being little to not at all affected by hot or wet weather or both, as to color and form, except at very high temperatures the color is less intense and the form of the petals is less recurled.

Before the calyx breaks the size is medium, form moderately pointed, frequently with one or more sepals having foliaceous parts extending beyond the apex of the calyx up to about three quarters of an inch, the number and size of the foliaceous parts being variable and frequently having one narrow, pointed, serrate appendage on one side of some of the sepals, and occasionally on both sides, otherwise the sepals are usually normal and regular, tapering to lanceolate at their apex, turning back nearly perpendicular to the pedicel and curved downward as the bud opens.

Color of the bud as the calyx and petals open, both sides of petals Rose Red [2] to Spectrum Red with a mild overlay of Lemon Yellow.

Bloom: As the flower opens and develops to maturity the color of the petals slowly change to Deep Rose Pink and the overlay of Lemon Yellow slowly disappears.

The flower is usually 3½ to 5 inches in diameter when fully open, infrequently more or less, petals vary around 25, frequently some smaller petals and petaloids in the center, variable in number.

The flower opens high centered, formal, recurled, showing stamens and pistils. The petals are variable from obovate to ovate to irregular and frequently with surfaces of petaloids variously warped and edges especially of the smaller petals frequently notably irregular. The larger petals often have two notches, one each side of a short apex that varies irregularly from acute to circular. Texture is medium to thick and leathery; both sides satiny; with slight veining which is not prominent. The time of opening in favorable conditions is two to three days.

The petals are substantial and after about five to six days drop off cleanly, except that occasionally one or two inner petals or petaloids cling to turn dull, to fall later. The flower does not "ball" in wet weather. The flower lasts well, is not affected at any stage by moderate cold or hot temperatures, or by humidity or wet weather.

Reproductive organs:

*Stamens*, quantity variable, lengths medium, slightly uneven, usually more than 100.

*Anthers*, Light Salmon Orange.

*Filaments*, nearly Mustard Yellow.

*Pistils* are several of slightly uneven length, averaging about one-half inch long.

*Ovaries* are usually all inclosed.

[2] This and other color references hereinafter, unless otherwise noted are to Robert Ridgway, Color Standards.

*Hips* frequently develop to ovoid to globular, color comparable with under side of leaves with variable colored overlay on the side exposed to the sun, moderately smooth; walls, thin, fleshy.

*Sepals* are persistent and break off easily.

*Seeds* variable in number.

*Plant*

Foliage: Is abundant, of compound leaves of three to five leaflets near the flower, five leaflets lower down the stem and frequently seven leaflets nearer the base. Size of leaflets medium, averaging on young plants in size a little larger than half way between the average hybrid tea and the *Rosa wichuraiana* leaflets. As the plants develop in size some of the leaflets develop to twice the size described above. Form of leaflets usually ovate with apex acute, base rounded frequently slightly acute, edges with serrations nearly regular and medium in size.

The color of the upper surface when the stem is in flower is Medium Dark Green to Forest Green, under side Bice Green.

The petioles are medium with several minute hairs on the upper sides or edges, and small prickles on the under sides, nearly straight, to slightly hooked toward the stem, all substantially the same color as the leaves, the prickles often tinged with Dahlia Carmine and the upper surface of petioles show overlay of Dahlia Carmine, more pronounced toward the base.

The stipules are medium long from about one half to three quarters of an inch long, medium width about one quarter inch wide, with pointed apexes the inner sides of which form an angle of about 90°. The edges have many very short minute hairs.

Stems are medium to large as the plant develops, color Bice Green, side toward sun frequently shaded with Dahlia Carmine, the pedicels notably so. The prickles are nearly Dahlia Carmine, turning to more colorless, usually two to three between leaves.

Growth: Habit is hybrid tea type of growth, to ascending by branching and growth from the base to climbing.

Winter resistance: From tests at Little Compton, Rhode Island, this new rose plant compares in winter resistance with that of the sub-zero hybrid tea, "Pink Princess" (Plant Patent 459).

Comparisons: I know of no *Rosa wichuraiana* hybrid tea that compares with this new rose. The nearest rose of hybrid tea type is the variety "M. B." which opens less recurled, less pointed, and has more petals, and lacks the lemon yellow overlay and is more formal. And the new rose can bear more flowers more constantly, under favorable conditions.

I claim:

The hardy hybrid *Rosa wichuraiana* hybrid tea rose plant variety herein disclosed, characterized by its resistance to winter injury, its mild pleasing fragrance, its leaflets of a brilliant green, with form and color substantially as described and shown, and its flower being of Red to Pink shades with Yellow overlay.

JOSEPHINE D. BROWNELL.

No references cited.